United States Patent
Mehtali et al.

(10) Patent No.: US 6,284,252 B1
(45) Date of Patent: Sep. 4, 2001

(54) TRANSDOMINANT TAT VARIANTS OF THE HUMAN IMMUNODEFICIENCY VIRUS

(75) Inventors: Majid Mehtali; Tania Sorg, both of Strasbourg (FR)

(73) Assignee: Transgene S.A., Strasbourg (FR)

(*) Notice: Subject to any disclaimer, the term of this patent is extended or adjusted under 35 U.S.C. 154(b) by 0 days.

(21) Appl. No.: 09/096,172

(22) Filed: Jun. 12, 1998

Related U.S. Application Data

(62) Division of application No. 08/177,145, filed on Jan. 4, 1994, now Pat. No. 5,889,175.

(30) Foreign Application Priority Data

Jan. 4, 1993 (FR) .................................................. 93 00004

(51) Int. Cl.$^7$ .................................................. A61K 39/21
(52) U.S. Cl. .................. 424/208.1; 530/300; 424/188.1; 435/69.1
(58) Field of Search ............................. 424/188.1, 208.1; 530/300; 435/69.1

(56) References Cited

PUBLICATIONS

Green et al., 1989, Cell 58: 215–23.*
Arya, S., 1993, Aids Res. Hum. Retro. 9:839–48.*
Pearson et al., 1990, PNAS, USA 87:5079–83.*

* cited by examiner

*Primary Examiner*—Laurie Scheiner
*Assistant Examiner*—Jeffrey S. Parkin
(74) *Attorney, Agent, or Firm*—Burns, Doane, Swecker & Mathis, L.L.P.

(57) ABSTRACT

The present invention relates to new variants of the human immunodeficiency virus (HIV) TAT protein which exhibit a transdominant phenotype, as well as to the DNA fragments encoding said variants, the expression cassettes permitting their expression by the recombinant route and the cells containing them. The transdominant variants of the TAT protein are especially useful for the prevention or treatment of HIV infections.

24 Claims, 5 Drawing Sheets

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: YES (vi) ORIGINAL SOURCE:
       (C) INDIVIDUAL ISOLATE: mutagenesis oligonucleotide (38Phe
           to Asp)

(xi) SEQUENCE DESCRIPTION: SEQ ID NO:1:

TAAAGCTTTT GTTGTGTCAC AAACTT                                              26

(2) INFORMATION FOR SEQ ID NO:2:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: YES (vi) ORIGINAL SOURCE:
       (C) INDIVIDUAL ISOLATE: mutagenesis oligonucleotide (TAT
           41Lys to Ala)

(xi) SEQUENCE DESCRIPTION: SEQ ID NO:2:

GCCTAAGGCT GCTGTTGTGA A                                                   21

(2) INFORMATION FOR SEQ ID NO:3:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: YES (vi) ORIGINAL SOURCE:
       (C) INDIVIDUAL ISOLATE: mutagenesis oligonucleotide (TAT
           54Gln to stop)

(xi) SEQUENCE DESCRIPTION: SEQ ID NO:3:

TCTTCGTCGT TATCTCCGCT T                                                   21

(2) INFORMATION FOR SEQ ID NO:4:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (vi) ORIGINAL SOURCE:
            (C) INDIVIDUAL ISOLATE: mutagenesis oligonucleotide (TAT
                40Thr to Ala)

(xi) SEQUENCE DESCRIPTION: SEQ ID NO:4:

TAAAGCTTTT GCTGTGAAAC                                                    20

(2) INFORMATION FOR SEQ ID NO:5:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (vi) ORIGINAL SOURCE:
            (C) INDIVIDUAL ISOLATE: mutagenesis oligonucleotide (TAT
                41Lys to Glu)

(xi) SEQUENCE DESCRIPTION: SEQ ID NO:5:

GCCTAAAGCT TCTGTTGTGA A                                                  21

(2) INFORMATION FOR SEQ ID NO:6:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (vi) ORIGINAL SOURCE:
            (C) INDIVIDUAL ISOLATE: mutagenesis oligonucleotide (TAT
                45Ile to Ser)

(xi) SEQUENCE DESCRIPTION: SEQ ID NO:6:

GCCATAGGAG GATCCTAAGG                                                    20

(2) INFORMATION FOR SEQ ID NO:7:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO

-continued

```
    (iv) ANTI-SENSE: YES (vi) ORIGINAL SOURCE:
         (C) INDIVIDUAL ISOLATE: mutagenesis oligonucleotide (TAT
             47Tyr to Arg)

(xi) SEQUENCE DESCRIPTION: SEQ ID NO:7:

TCCTGCCTCT AGAGATGC                                                         18
```

TRANSDOMINANT TAT VARIANTS OF THE HUMAN IMMUNODEFICIENCY VIRUS

This application is a divisional of U.S. application Ser. No. 08/177,145, filed Jan. 4, 1994, now U.S. Pat. No. 5,889,175, the contents of which are incorporated herein by reference.

The subject of the present invention is new variants of the TAT protein of the human immunodeficiency virus (HIV), as well as the DNA fragments encoding said variants, the expression cassettes which permit their expression by the recombinant route and the cells containing said expression cassettes. The TAT protein variants, the cassettes and the cells are especially useful for the prevention or treatment of HIV infections.

Acquired immunodeficiency syndrome (AIDS) develops following infection of the T4 lymphocytes of an individual by the HIV virus. The infection may be asymptomatic for many years, but as soon as the cells are activated, the HIV virus replicates rapidly and destroys them. AIDS is characterized by a deficiency of the cellular immunity which has the effect of making the individual particularly sensitive to any opportunistic infection. In July 1992, WHO recorded 501,272 AIDS cases worldwide. (AIDS Information international literature on acquired immunodeficiency syndrome and related retroviruses, 1992, 8, Leeds University Press, Editor A. W. Boylston, Leeds). But these figures are however lower than the reality since this disease constitutes a real epidemic in certain African countries.

AIDS remains a disease whose mortality rate was still very high in 1992. indeed, 90% of people die within the two years following the onset of AIDS. Up until now, no treatment has proved to be totally satisfactory in spite of the many efforts invested. The development of effective treatments has been hampered by the specific complexity of the HIV virus.

HIV is a retrovirus which belongs to the family of lentiviruses. Like any retrovirus, HIV in formed of an envelope surrounding a capsid of protein nature, which contains the genetic material consisting of an RNA molecule associated with various viral proteins which are necessary for the first stages of the replicative cycle.

After infection of a T lymphocyte, the RNA molecule is copied by the viral reverse transcriptase into DNA. The DNA is integrated into the cellular genome and constitutes what is commonly called a provirus. The proviral DNA can stay there in the latent state or can be transcribed into RNA by the cellular machinery to produce on the one hand viral genomic RNA and on the other hand messenger RNAs (mRNA) which will be translated into viral proteins.

The formation of new viral particles or virions occurs by encapsulation of the viral genomic RNA into the capsid. The particle thus formed is detached from the cell by budding taking along a portion of the cellular membrane, into which the viral envelope glycoprotein is incorporated. The virions thus liberated are capable of infecting other lymphoid cells by virtue of a specific and mutual recognition of the $CD_4$ receptor expressed at the surface of the T4 lymphocytes and of the HIV envelope protein.

BRIEF DESCRIPTION OF DRAWINGS

Generally, the HIV genome comprises, as indicated in FIG. 1:

3 structural genes: gag, pol and env encoding the capsid, envelope and reverse transcriptase proteins respectively, at least 6 genes: tat, rev, nef, vif, vpr and vpu, which encode proteins probably having regulatory functions which are still poorly defined in the case of some, and the cis-regulatory sequences which are essential for transcription, localized at both 5' and 3' ends of the proviral DNA at the level of the LTRs (Long Terminal Repeat). The 5' LTR contains the promoter sequences and the regulatory elements required for initiation of transcription, whereas the 3' LTR is involved in termination of transcription. In addition, the transcription of the viral genes is subjected to a complex regulation which is controlled especially by the viral proteins TAT and REV.

Figure 1:
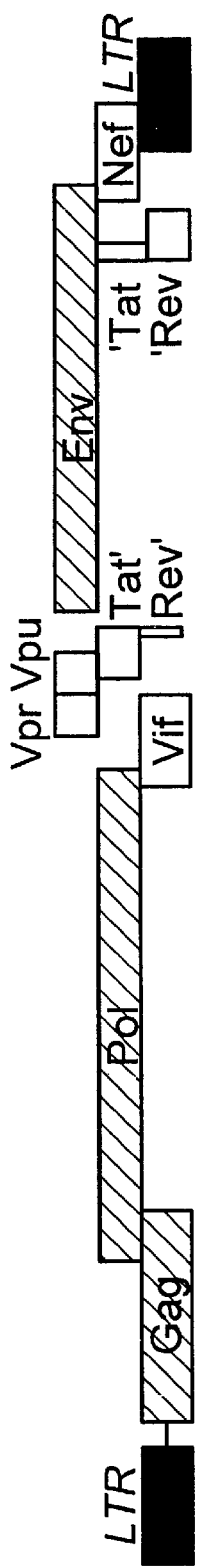

The TAT protein is a regulatory protein which is expressed early during the viral cycle. Its site of action is the nucleus. Its role consists in transactivating the expression of the genes encoding all the HIV proteins. The TAT protein interacts specifically with a short nucleotide sequence of the viral genome: the TAR sequence (Trans-Activation Responsive Region) which is localized at the 5' end of the HIV genome between nucleotides (nt) −17 to+80 of the 5' LTR. This sequence is therefore partially present in all viral mRNAs. It is assumed that the TAT-TAR complex, probably in association with other cellular factors, favors the transcription of the viral genes, stabilizes the mRNAs thus obtained and improves the translation of these mRNAs into proteins. Thus, the virus multiplies very rapidly as soon as the tat gene is activated.

It has been possible to evaluate in vitro the effect of TAT protein-induced transactivation using an indicator gone whose expression can be easily measured, such as the CAT (Chloramphenicol Acetyl Transferase) gene. The CAT gene, placed under the control of the 5' LTR of the HIV virus including the TAR sequence, has been introduced into animal cells by transfection. In cells which do not express TAT, for example cells not infected by the HIV virus, the transcription of the CAT gone from the viral promoter is blocked or reduced to a minimum, such that no or very little CAT gene product is detected, whereas in the presence of the TAT protein, an increase in the gene expression by a factor of 100 to 1000 is observed according to the calls, which results from an acceleration of transcription associated with an improved efficiency of translation.

The HIV transactivator gene tat comprises 2 coding exons. The first is situated in the central region of the genome, between the sequences encoding the pol and env genes, and encodes for most of the protein, namely the 72 N-terminal amino acids. The second, which encodes only the 14 C-terminal amino acids is not essential for biological activity.

The structure of the TAT protein is suggested by its function. It should comprise at least one domain which permits activation of the transcription of the viral genes, called activation domain, a domain for binding to the TAR nucleotide sequence, its target sequence, and a domain which permits its nuclear localization.

Numerous studies have shown that the TAT protein consists of 5 domains (FIG. 2):

a first domain (amino acids 1 to 37) possesses a cysteine-rich sequence whose function is still unknown. Some studies suggest that this region participates in the folding of the protein and in the dimerization of the TAT molecules and is thought to protect it against proteases, the domain consisting of amino acids 38 to 48 corresponds to the first activation domain, the domain consisting of amino acids 49 to 57 possesses the sequences for nuclear localization and for attachment to the TAR element, the domain consisting of amino acids 58 to 72 corresponds to the second TAT activation domain, the domain consisting of amino acids 73 to 86 is not essential for the TAT activity.

Most HIV-related retroviruses possess transactivating genes which encode proteins capable of activating the transcription of the viral genes from the LTRs. In the past few years, numerous variants of these Transactivating proteins derived from different types of viruses have been described, and among them negative and dominant variants (Wachsman et al., Science, 1987, 235, 674–677; Friedman et al., Nature, 1988, 335, 452–454), designated hereinafter transdominant variants.

The transdominant variants have been defined as variants which have a reduced capacity for inducing activation of the expression of the genes placed under the control of the viral promoter (reduced transactivating activity) but which have the capacity to recognize their target sequence situated at the level of this promoter, such that they can competitively inhibit the function of the native transactivating protein.

Since these variants interfere in a dominant manner with the function of the native proteins, they could constitute a new class of antiviral agents capable of promoting"intracellular immunization" of the infected cells.

Generally, this technology consists in genetically modifying cells so as to make them synthesize a protein or nucleic acids conferring a specific advantage on them, such as for example according to the concept defined by D. Baltimore (Nature, 1988, 335, 395–396), a resistance against infection by a given virus, such as the HIV virus.

Thus, Green et al. (Cell, 1989, 58, 215–233) have generated transdominant variants modified in the first activation domain of the HIV virus TAT protein. These authors disclose 4 variants derived from a peptide fragment of the TAT protein: two of them are described as being effective transdominants, namely the variants TAT (Lys$^{41}$→Ala) and TAT (Ty$^{47}$ →Ala) and the other two are moderate transdominants, namely TAT (Ser$^{46}$→Ala) and the double variant TAT (Ser$^{46}$, Tyr$^{47}$→Ala, Ala).

Nevertheless, the variants mentioned in this publication appear to be disputed (Frankel et al., Proc. Natl. Acad. Sci. USA, 1989, 86, 7397–7401). The Applicant has also tried to reproduce the results obtained with the variant (Lys$^{41}$→Ala), but unsuccessfully, as indicated hereinafter.

Moreover, Pearson et al. (Proc. Natl. Acad. Sci. USA, 1990 87, 5079–5083) show the importance of the Region consisting of amino acids 48 to 54 in the production of a transdominant phenotype. Indeed, the replacement of the codon encoding glutamine (Gln) in position 54 by a stop codon generates a truncated variant ΔTAT which exhibits such a phenotype.

New variants of the HIV TAT protein have now been found which exhibit a transdominant phenotype and which have been modified at the level of certain residues of the activation domains.

These variants are especially useful within the framework of an anti-AIDS therapy since they exhibit a reduced transactivating activity and interfere in a dominant manner with the function of the native TAT protein. These new variants could constitute antiviral agents effective for inhibiting the replication and propagation of the HIV virus. Indeed, the action of these transdominant variants is thought to occur from the first infection cycle even before the virus has been able to synthesize the proteins and the RNA necessary for the formation of new viral particles.

The subject of the present invention is therefore a transdominant variant of the HIV virus TAT protein or of a functional fragment of said protein which comprises at least one mutation; said mutation being characterized by the presence of an amino acid residue different from the natural residue in position 38, 40, 41, 45 or 47, on the condition, however, that the amino acid in position 41 is different from alanine or threonine and that the amino acid in position 47 is different from alanine or histidine.

Generally, there is agreement to describe the sequence of a variant of the TAT protein on the basis of the sequence of the TAT protein of the HIV1 virus Lai isolate, as disclosed by Wain-Hobson et al. (Cell, 1985, 40, 9–17).

Nevertheless, the TAT protein and the DNA fragment which encodes the TAT protein were originally described from the viral strain HIV1, Lai isolate. However, the viral strains and the viral isolates described within the same strain exist in large numbers. Furthermore, a particular virus is susceptible to variability during its propagation. Consequently, the DNA fragment which encodes the TAT protein may have a nucleotide sequence which is different from one virus to another. Likewise, the TAT protein may have an amino acid sequence which is different from one virus to another. But the common denominator is the function of the protein which is to transactivate the expression of the genes placed under the control of a prom ter containing a TAR target sequence, such as the HIV virus promoter included in the 5' LTR of the viral genome. By HIV TAT protein, there is understood any protein giving a transactivation result which is substantially identical to that exhibited by the TAT protein of the HIV1 virus Lai isolate.

In practice, the sequence of a variant of the TAT protein is aligned with that of the HIV1 virus TAT protein. The numbering of the amino acids in the sequence of a variant of the TAT protein will therefore be based on that established for the HIV1 virus TAT protein. Thus, an amino acid residue in position, for example, 41 in the sequence of a variant of the TAT protein is in fact an amino acid residue which corresponds, after alignment, to the amino acid in position 41 in the sequence of the HIV1 virus native TAT protein.

More particularly, a TAT protein variant according to the invention exhibits especially a transdominant phenotype characterized by a transactivating activity of less than about 50% compared with that of the native TAT protein, advantageously lose than 20% and preferably less than 10% and a native TAT function-inhibitory activity, as determined for a concentration ratio variant/native TAT of 10/1, greater than 50%, advantageously greater than 75% and preferably greater than 90%. Various methods for the measurement of transactivating activity are currently known. They vary according to the reporter gene used. By way of example, there may be mentioned the method using the CAT gene placed under the control of the 5' LTR of the HIV virus, which method is described in the examples hereinafter.

A TAT protein variant according to the invention can be derived from a functional fragment of said protein and can be mutated at the level of a residue as indicated hereinbefore, the numbering of the amino acids being also aligned with that established for the reference HIV1 virus native TAT protein. By functional fragment of the TAT protein, there is understood any fragment of said protein which is capable of inducing a transactivation of the expression of the genes placed under the control of a promoter containing the TAR sequence, such as the HIV virus promoter. For example, a TAT protein variant according to the invention can be generated after mutation of a fragment of the TAT protein, such as a fragment starting with amino acid 1 and stopping at amino acid 72.

A TAT protein variant according to the invention may contain several mutations compared with the HIV native TAT protein. It may contain a combination of at least 2 mutations as described hereinbefore.

More particularly, a TAT protein variant according to the invention has especially a sequence whose degree of homology with the HIV1 native TAT sequence is greater than 75%, advantageously greater than 90% and preferably greater than 95%.

Of course, the residues to be mutated can be replaced by any amino acid other than the natural residue, except the residue in position 41 which can be replaced by an arginine, asparagine, aspartic acid, cysteine, glycine, glutamic acid, glutamine, histidine, isoleucine, leucine, methionine, phenylalanine, proline, serine, tryptophan, tyrosine and valine; and the residue in position 47 which can be replaced by an arginine, asparagine, aspartic acid, cysteine, glycine, glutamic acid, glutamine, isoleucine, leucine, lysine, methionine, phenylalanine, proline, serine, threonine, tryptophan and valine.

According to a particularly advantageous aspect of the invention, a TAT variant is selected from:

(1) a variant comprising in position 38 an amino acid having an acidic side chain such as glutamic acid, aspartic acid or preferably, aspartic acid, (2) a variant comprising in position 40 an amino acid having a non-polar side chain such as alanine, valine, leucine, isoleucine, proline, phenylalanine, methionine, tryptophan or preferably, alanine, (3) a variant comprising in position 41 an amino acid having an acidic side chain such an glutamic acid, aspartic acid or preferably, glutamic acid, (4) a variant comprising in position 45 an amino acid having an uncharged polar side chain such as glycine, asparagine, glutamine, cysteine, serine, threonine, tyrosine or preferably, serine, (5) a variant comprising in position 47 an amino acid having a basic side chain such as lysine, arginine, histidine or preferably, arginine.

(6) a variant comprising in position 59 an amino acid having an uncharged polar side chain such as glycine, asparagine, glutamine, cysteine, serine, threonine, tyrosine or preferably, glycine, (7) a variant comprising in position 60 an amino acid having a non-polar side chain such as alanine, valine, leucine, isoleucine, proline, phenylalanine, methionine, tryptophan or preferably, tryptophan, (8) a variant comprising in position 61 an amino acid having a basic side chain such as lysine, arginine, histidine or preferably, arginine, (9) a variant comprising in position 62 an amino acid having a non-polar side chain such as alanine, valine, leucine, isoleucine, proline, phenylalanine, methionine, tryptophan or preferably, alanine,

(10) a variant comprising in position 63 an amino acid having an uncharged polar side chain such as glycine, asparagine, glutamine, cysteine, serine, threonine, tyrosine or preferably, serine,

(11) a variant comprising in position 64 an amino acid having a non-polar side chain such as alanine, valine, leucine, isoleucine, proline, phenylalanine, methionine, tryptophan or preferably, leucine,

(12) a variant comprising in position 65 an amino acid having a non-polar side chain such as alanine, valine, leucine, isoleucine, proline, phenylalanine, methionine, tryptophan or preferably, leucine,

(13) a variant comprising in position 66 an amino acid having an uncharged polar side chain such as glycine, asparagine, glutamine, cysteine, serine, threonine, tyrosine or preferably, tyrosine,

(14) a variant comprising in position 67 an amino acid having a basic side chain such as lysine, arginine, histidine or preferably, arginine,

(15) a variant comprising in position 68 an amino acid having an uncharged polar side chain such as glycine, asparagine, glutamine, cysteine, serine, threonine, tyrosine or preferably, asparagine,

(16) a variant comprising in position 69 an amino acid having a basic side chain such as lysine, arginine, histidine, or preferably, arginine,

(17) a variant comprising in position 70 an amino acid having an uncharged polar side chain such as glycine, asparagine, glutamine, cysteine, serine, threonine, tyrosine or preferably, glutamine,

(18) a variant comprising in position 71 an amino acid having an uncharged polar side chain such as glycine, asparagine, glutamine,. cysteine, serine, threonine, tyrosine or preferably, threonine,

(19) a variant comprising in position 72 an amino acid having a non-polar side chain such as alanine, valine, leucine, isoleucine, proline, phenylalanine, methionine, tryptophan or preferably, leucine.

The invention also relates to a DNA fragment encoding said TAT protein variant. The sequence encoding a TAT protein variant can be obtained according to conventional genetic engineering techniques, for example by site-directed mutagenesis. Thus, the DNA fragment comprising the gene encoding the HIV native TAT protein or a portion of said sequence is cloned into an M13 type phage. The sequence is modified using an appropriate oligonucleotide, so as to obtain the desired mutation(s).

The invention also includes an expression cassette comprising a DNA fragment encoding a TAT protein variant according to the invention, placed under the control of appropriate elements which permit its expression. An expression cassette is especially useful in order to make it possible to synthesize a TAT protein variant in a heterologous expression system or alternatively as an element of a vector intended for gene therapy such as a retroviral or adenoviral vector. By appropriate elements which permit the expression of the DNA fragment encoding a TAT protein variant, there is understood all the elements which permit the transcription of said DNA fragment into mRNA and the translation of the mRNA into protein.

These elements contain especially an appropriate promoter. Within the context of the invention, the term "promoter" means any transcriptional control element involved in the expression of a DNA fragment according to the host cell which has been retained. Such control elements are well known to persons skilled in the art and are inserted into the expression cassette by conventional genetic engineering techniques.

The retained promoter may be of cellular or viral origin. The promoter may be of the ubiquitous type which permits a permanent expression of the DNA fragment. Such is the case for the PGK (phosphoglycerate-kinase) promoter which is functional in yeast or the late promoter of the SV40 virus (Simian Virus 40), the promoter of the EKG (Hydroxy-Methyl-Glutaryl coenzyme A reductase) gene, the promoter of the thymidine kinase (TK) gene of the Herpes simplex virus type 1 (HSV1), the promoter EIII and MLP (Major Late Promoter) of adenovirus and the LTR of the MoMuLV virus (Moloney Murine Leukemia Virus) which are functional in animal calls.

The term"promoter" also includes a regulatable type promoter, for example a tissue-specific promoter such as the immunoglobulin gone promoter which is specific for lymphocytic cells.

In addition, the expression cassette may contain:
(1) UASs (Upstream Activating Sequence) such as the UASs of the yeast GAL4 (Galactose) gene,
(2) enhancers which may be placed either upstream of the promoter or downstream of the DNA fragment and which make it possible to increase the levels of expression, such as the enhancer of the human CD2 gene. Furthermore, the latter comprises elements which make it possible to selectively target the expression of the DNA fragment in T-type lymphocytic cells,
(3) intervening sequences known to improve gene expression in higher eukaryotes, such as the intron of the SV40 virus,
(4) splicing signals such as for example those of the SV40 virus which permit removal of the intervening sequences from mRNAs intended to be translated into proteins,
(5) elements involved in the termination of transcription, such as the polyadenylation signals of the SV40 virus.

Generally, the expression cassette can permit the expression of a TAT protein variant inside a host cell, and preferably inside a lymphocyte.

The expression cassette can also permit the production of the TAT protein variant in the culture medium from which it can easily be harvested, In this case, the DNA fragment encodes a precursor of the TAT protein variant comprising, upstream of the mature sequence, a signal peptide which permits secretion of said variant from the host cell. Such signal peptides are well known to persons skilled in the art, for example the signal sequence of the yeast Mat alpha factor.

The expression cassette is inserted into an expression vector which is used to transform a host cell in which the promoter and the appropriate elements are functional. Such a vector may be in the form of a plasmid or a viral vector, for example a retroviral vector derived from MoMuLV or an adenoviral vector derived from type 5 adenovirus.

The present invention extends to the cells comprising an expression cassette according to the invention, it being possible for the cells to be of eukaryotic or prokaryotic origin. The host cell may be a bacterium, a fungus, for example a yeast or a mammalian cell. Preferably, the host cell will be a human cell of the hematopoietic line.

The invention also relates to a process for the preparation of a TAT protein variant according to the invention, according to which:
(1) a eukaryotic or prokaryotic cell according to the invention, containing a DNA fragment encoding said variant, is cultured in an appropriate culture medium, and
(2) the variant is harvested from the culture medium or from said cell.

The invention also covers a TAT protein variant obtained using said process.

The invention also extends to the therapeutic use of a TAT protein variant according to the invention, of an expression cassette or of a cell producing said variant to inhibit the replication of the HIV virus. Preferably, the present invention relates to the use of a TAT protein variant or of an expression cassette or of a cell producing said variant for the manufacture of a medicinal product intended for the treatment or prevention of AIDS in mammals, preferably humans.

Advantageously, an expression cassette or a cell according to the invention, may be used for the purpose of anti-AIDS gene therapy. The expression cassette is inserted into a retroviral type vector which is introduced into the stem cells of the hematopoietic line which are collected from the bone marrow of an individual (preferably infected with HIV). The stem cells thus transfected are reinjected into the donor. They are capable of dividing and becoming differentiated, inter alia, into lymphocytes. The lymphocytes which comprise the retroviral vector will express over a prolonged period of time the gene encoding a transdominant variant of the TAT protein, rendering said cells resistant to HIV infection.

The invention also relates to a pharmaceutical composition comprising as therapeutic or prophylactic agent a variant according to the invention, an expression cassette or a cell producing such a variant. A pharmaceutical composition according to the invention can be prepared according to the techniques in common usage. For example a, an acceptable carrier, diluent or adjuvant is combined with the therapeutic or prophylactic agent in a therapeutically effective quantity.

Finally, the invention relates to a method of treatment according to which a therapeutically effective quantity of a TAT protein variant according to the invention, an expression cassette or a cell producing such a variant is administered to a patient.

The invention is illustrated below with reference to the following figures:

FIG. 1 is a schematic representation of the HIV virus genome, the genes encoding the proteins being represented according to the reading frame used; LTR: black boxes; genes encoding the structural proteins: gray boxes, genes encoding the regulatory proteins: white boxes.

Figure 2:
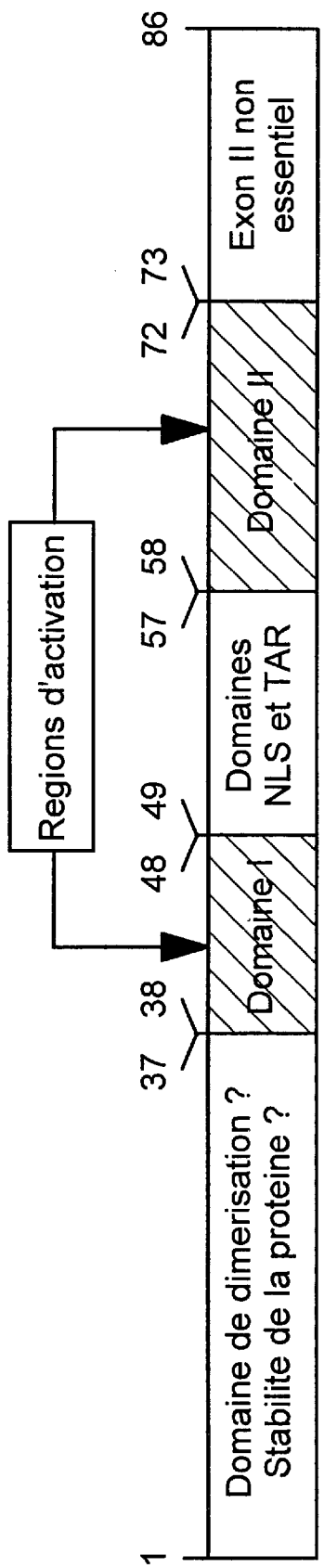

FIG. 2 is a schematic representation of the different domains which constitute the HIV virus native TAT protein, the amino acids which constitute each domain being indicated above each of the domains.

Figure 3:
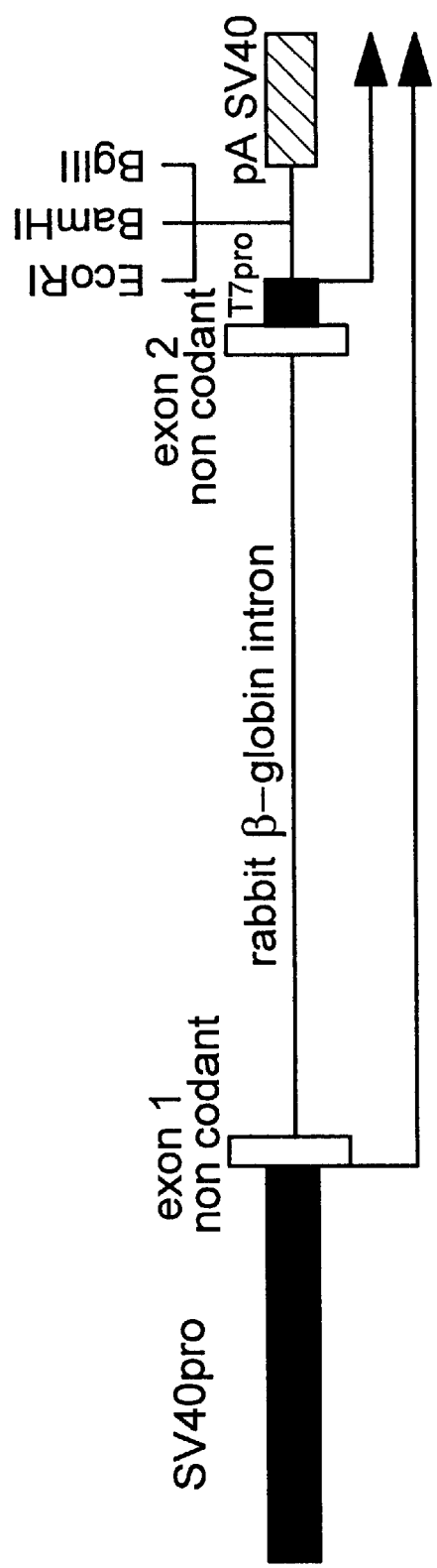

FIG. 3 is a schematic representation of the eukaryotic expression vector pSG5 which comprises in sequence: the SV40 promoter (SV40 pro; black box), the 3' fragment of the non-coding exon 1 of the rabbit β-globin gene (white box), the intron of the rabbit β-globin gene (continuous line), the non-coding beginning of exon 2 of the rabbit β-globin gene (white box), the T7 bacteriophage promoter (T7 pro; black box), the unique EcoRI, BamHI and BglII sites which permit the cloning of a gene of interest and the polyadenylation signal of the SV40 virus (pA SV40; gray box).

Figure 4:
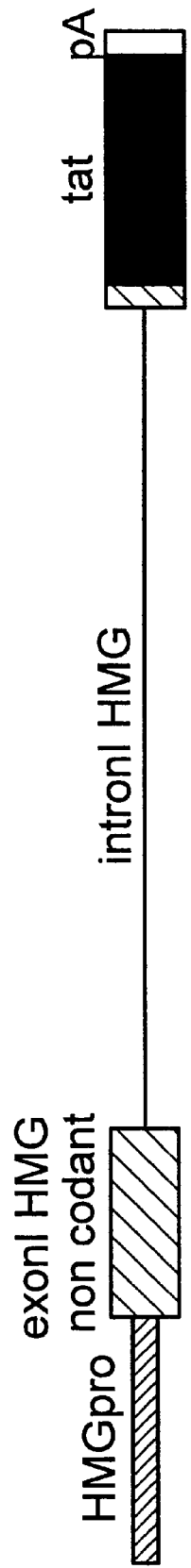

FIG. 4 is a schematic representation of the native TAT protein expression vector pHMG-Tat which comprises in sequence: the promoter of the HMG gene (HMG pro), the non-coding exon 1 of the HMG gene (shaded box), intron 1 and the acceptor site for the splicing of the MM gene, the copy DNA encoding the 86 amino acids of the TAT protein (black box) and the SV40 polyadenylation signal (pA, white box).

Figure 5:
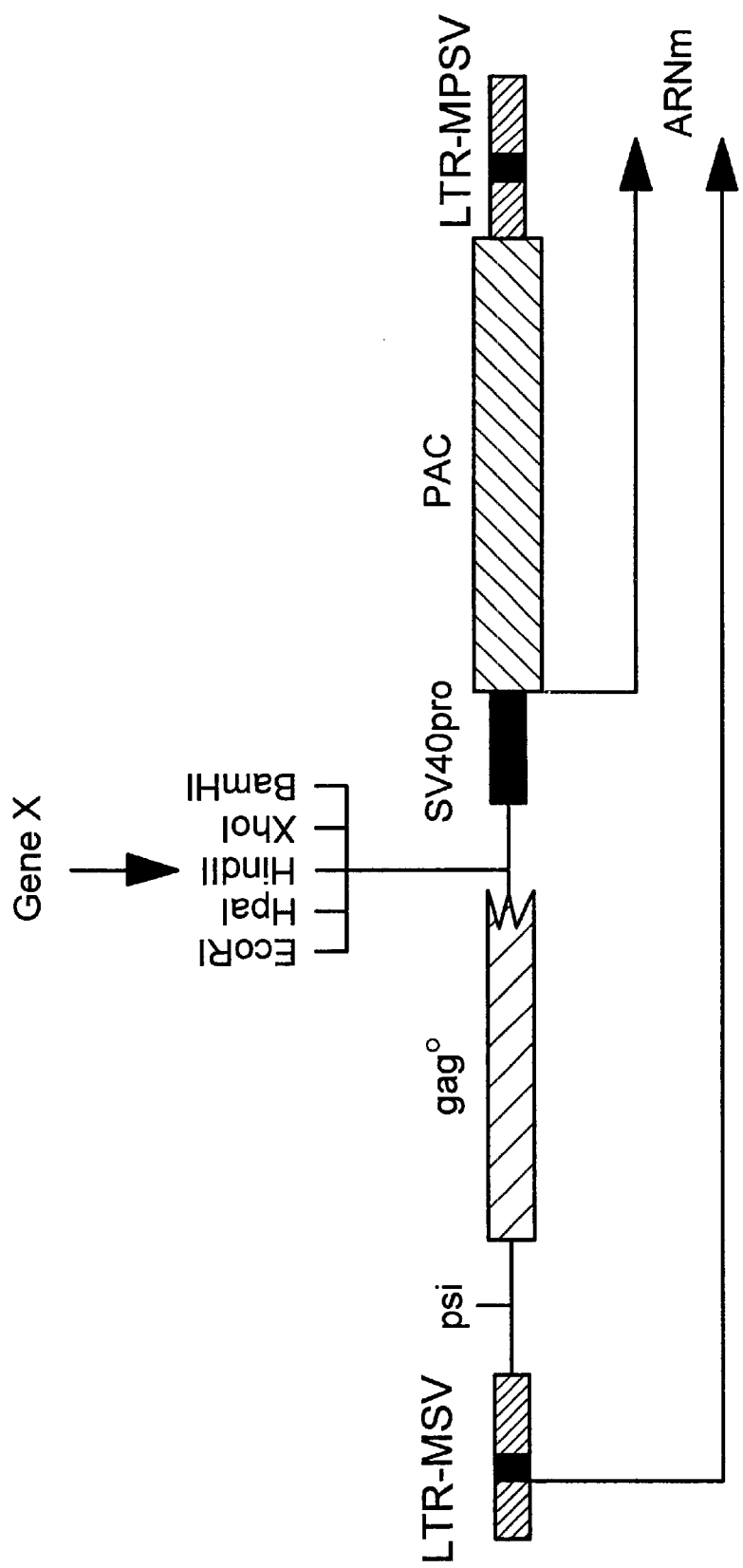

FIG. 5 is a schematic representation of the retroviral vector pLXSP comprising in sequence the 5' LTR of the HSV virus (Murine Sarcoma virus) including the viral promoter region, an encapsulation region (psi), the 5' portion of the viral gag gene (gag°), multiple cloning sites which permit the insertion of heterologous genes (gene x), the SV40 virus promoter directing the expression of the puromycin resistance gene (PAC) and the 3' LTR of the MPSV virus (Myelo Proliferative Sarcoma Virus) including the polyadenylation signals.

EXAMPLES

Example 1

Construction of the expression plasmid pTG23321 expression of the variant TAT (Phe$^{38}$→Asp) and characterization of the transdominant phenotype.

A DNA fragment containing the copy DNA corresponding to the 2 exons of the tat gone of the HIV-Lai isolate genome (Wain-Robson et al., Cell, 1985, 40, 9–17; Sodroski et al., Science, 1985, 229, 74–77) was modified in order to create a BamHI in 5' of the initiator ATG. In addition, a BamHI site exists naturally, 53 bp after the stop codon of the tat gene. The 300 bp BamHI fragment containing the non-mutated tat gone was purified by means of the Gene Clean kit (Bio 101, Inc, P.O. Box 2284, La Jolla) and inserted into a vector M13TG130 (Kieny et al., Gene, 1983, 26, 91–99) so as to give the vector M13TG2306, on which the mutageneses are performed.

The mutation of the codon encoding residue 38 is on M13TG2306, using the Amersham kit (Oligonucleotide-directed in vitro mutagenesis system, version 2.1 RPN 1523) and using the oligonucleotide described in the Sequence identifier SEQ ID NO:1.

The oligonucleotide was designed so as to replace the codon encoding the phenylalanine (Phe) residue in position 38 by an aspartic acid (Asp) and also to create a HindIII restriction site at the level of the codon encoding the residue in position 42 of the TAT sequence without modifying the amino acid which it encodes. The presence of a restriction site makes it possible to identify easily the mutated vectors from the parentals during analysis of the bacteriophage DNAs by the mini-preparation technique described by Maniatis et al. (Molecular cloning: a laboratory manual, 1989, Cold Spring Harbor Laboratory).

After mutagenesis, the BamHI fragment containing the mutated tat gene is then transferred into the eukaryotic expression vector pSG5 (Green et al., Nucleic Acids Res, 1988, 16, 369) illustrated in FIG. 3. The Resulting plasmid, pTG2332, permits expression of the variant TAT (Phe$^{38}$→Asp).

The transdominant TAT variants of the prior art, the variant TAT (Lys$^{41}$→Ala) and ΔTAT (Gln$^{54}$→stop) respectively, were created by site-directed mutagenesis of the vector M13TG2306, using the oligonucleotides respectively described in SEQ ID NO:2 making it possible to modify the codon encoding the lysine residue in position 41 by an alanine and, in SEQ ID NO:3 making it possible to create a stop codon in place of the codon encoding the glutamine residue in position 54.

After mutagenesis, the mutated tat gene is inserted into the eukaryotic expression vector pSG5, giving respectively pTG2351 which permits the production of the mutant TAT (Lys$^{41}$→Ala) and PTG2352 which, permits the production of ΔTAT These prior art mutants are useful as a positive control for transdominance. Their transactivating activity as well as their capacity to inhibit the native TAT protein, is evaluated according to conditions which are strictly identical to those used for the TAT variants according to the invention and which are described below.

The transactivating activity of the variant TAT (Phe$^{38}$→Asp) is evaluated by transient transfection into HeLa calls of the expression vector pTG2332 with the reporter vector LTR-CAT (Emerman et al., EMBO J., 1987, 6, 37–55). The cells are transfected according to the calcium phosphate technique (Maniatis et al., Molecular cloning: a laboratory manual, 1989, Cold Spring Harbor Laboratory). Other procedures which make it possible to introduce a nucleic acid into a cell can also be used, such as the dextran sulfate technique, electroelution, methods based on osmotic shocks or microinjection into a selected cell.

The human HeLa cells are cultured at 37° C. In the presence of 5% $CO_2$ in MEM medium (Eagle's minimum, essential medium) supplemented with 10% fetal calf serum, 1% non-essential amino acids, 1% glutamine and 1% gentamycin.

The plasmid DNAs are purified on a cesium chloride gradient. 1 μg of pTG2332 and 0.5 μg of the plasmid LTR-CAT are transfected into the HeLa cells in culture, and plated at the rate of 4×10$^5$ cells per dish. The transfection of 1 μg of pHMG-Tat (FIG. 4) and 0.5 μg of LTR-CAT constitute the positive control for transactivation. The vector pHMG-tat is derived from the cloning of the BamHI fragment comprising the copy DNA of the tat gene encoding the 86 amino acids of the TAT protein, into the BamHI s of the vector pHMG (Mehtali et al., Gene, 1990, 91, 179–184). The plasmid DNAs to be transfected are taken up in 420 μl of TE (10 mM Tris-HCl, pH 7.5; 1 mM EDTA) and mixed with 60 μl of 2M $CaCl_2$. The mixture is added to 480 μl of 2x HBS (280 mM NaCl; 50 mM HEPES: 1.5 mM $Na_2HPO_4.2H_2O$ adjusted to pH 7.12 with NaOH) while shaking the tube gently. After 15 min, the precipitate is poured dropwise over the cells. The medium is changed 24 h after the transfection in order to remove excess precipitate. The cellular extracts are analyzed 48 h after the transformations in order to evaluate the expression of the CAT gene.

The HeLa cells are recovered by scraping into a CAT buffer (150 mM Tris-HM pH 8; 60 mM KCl; 15 mM NaCl; 2 mM EDTA, 0.15 mM spermine; 1 mM dithiothreitol (DTT); 0.4 mM phenylmethylsulfonyl fluoride (PMSF). 3 freeze-thaw cycles are performed in liquid nitrogen followed by incubation at 37° C. for 4 min. The lysate thus obtained is incubated at 65° C. for 10 min and centrifugation is performed at 10,000 rpm for 10 min so as to remove the cellular debris. The supernatant is recovered an which the protein concentration is determined by a Biorad colorimetric test.

15 μl of cellular extract optionally diluted and adjusted to 800 μl with $H_2O$ and 200 μl of Biorad reagent in $H_2O$ are incubated at room temperature for 10 to 60 min. The protein concentration is determined by measuring the optical density at 595 nm in relation to a bovine serum albumin calibration series.

The expression of the CAT gen is determined on an aliquot of extract corresponding to 10 to 20 μg of proteins. An adequate volume of cellular extract previously adjusted to 300 μl with 0.25 M Tris-HCl buffer, pH 7.8, is incubated with 32 μl of 5 mM acetyl coenzyme A and 20 μl (0.5 μCi) of $^{14}$C-chloramphenicol at 37° C. for 1 h 30 min. After extraction with ethyl acetate and centrifugation at 10,000 rpm for 5 min, the upper phase is freeze-dried. The latter is taken up in 15 μl of ethyl acetate, deposited onto a 60F$_{234}$ silica gel plate (Merck) and analyzed by thin-layer chromatography (migration in a buffer chloroform/methanol 19/1 for 1 h 30 min). The chromatogram is visualized by autoradiography and the bands corresponding to acetylated chloramphenicol are cut out. The radioactivity level is evaluated by scintillation counting. The percentage of transactivating activity of the mutant is calculated relative to the level measured with the positive control (pHMG-Tat+LTR-CAT), the latter representing 100% transactivating activity.

The transdominant activity of the variant TAT (Phe38→Asp) is evaluated by measuring its capacity to inhibit the transactivating function of the native TAT protein. The transdominant activity is determined by transient transfection into HeLa cells of the expression vector pTG2332 with the reporter vector LTR-CAT and the native TAT protein expression vector pHMG-Tat. 10 µg of pTG2332, 1 µg of pHMG-Tat and 0.5 µg of LTR-CAT are co-transfected according to the procedure described above.

48 h after the transfection, the cellular extracts are prepared and their protein concentration determined. An aliquot of extract corresponding to 10 to 20 µg of protein is subjected to the CAT assay. The technical conditions used have been described in detail above. The percentage inhibition of the native TAT protein by the variant TAT (Phe$^{38}$→Asp) is calculated relative to the positive control for activation resulting from the co-transfection of pHMG-Tat and LTR-CAT which represents 0%. The results obtained are reported in Table 1.

| Expression vector | Amino acid modification | TA$^{(1)}$ | TD$^{(2)}$ |
|---|---|---|---|
| pTG 2332 | Ph → Asp in position 38 | 1.4% | 98.0% |
| pTG 2333 | Thr → Ala in position 40 | 15.6% | 83.0% |
| pTG 2340 | Lys → Glu in position 41 | 3.0% | 97.0% |
| pTG 2358 | Ile → Ser in position 45 | 47.0% | 62.5% |
| pTG 2348 | Tyr → Arg in position 47 | 56.0% | 78.0% |
| pTG 2351 | Lys → Ala in position 41 | 172.0% | 0.0% |
| pTG 2352 | Gln → Stop in position 54 | 28.0% | 92.0% |
| pHMG Tat | Native TAT protein | 100.0% | 0.0% |

$^{(1)}$: Transactivating activity.
$^{(2)}$: Native TAT protein-inhibiting activity or trans-dominant activity.

The variant TAT (Phe$^{38}$→Asp) is an effective transdominant mutant since its transactivating activity is tiny (expression of the CAT gone evaluated at 1.4% relative to that measured with native TAT protein) and since it strongly inhibits the activity of the native TAT protein (98% inhibition in the presence of pTG2332).

It can be observed that the variant TAT (Lys$^{41}$→Ala) ascribed by Green et al., and which is thought to possess a transdominant phenotype according to the authors, gives completely contradictory results in these experiments. Indeed, it exhibits a particularly high transactivating activity (172%) and therefore appears to act in cooperation with the native TAT protein. In addition, this variant exerts no dominant effect on the native TAT function (0% transdominant activity).

The prior art variant ΔTAT produced by pTG2352 effectively constitutes a control for transdominance, confirming the validity of these experiments. it inhibits the transactivating activity of the native TAT protein by 92%. Nevertheless, this variant is capable of inducing an expression of the CAT gene placed under the control of the HIV LTR (28%), the transactivation being however less than that measured with the positive control pHMG-Tat.

Example 2

Construction of the expression vector PTG2333, expression of the variant TAT (Th$^{40}$→Ala) and characterization of the transdominant phenotype.

The vector M13TG2306 is subjected to a site-directed mutagenesis in order to replace the codon encoding the threonine (Thr) residue in position 40 of the HIV TAT protein by a codon encoding an alanine (Ala) residue and to introduce silent mutations so as to create a HindIII restriction site at the level of the codon encoding residue 42 which permits a rapid identification of the mutated vectors. The oligonucleotide used is described in SEQ ID NO:4. The mutated tat gene is transferred into the vector pSG5 giving rise to pTG2333 which makes it possible to produce the variant TAT (Thr$^{40}$→Ala).

The vector pTG2333 is transiently co-transfected into HeLa cells with the vector LTR-CAT in order to determine the transactivating activity of the variant TAT (Thr$^{40}$→Ala) according to the procedure described above. At the same time, its transdominant activity is determined by co-transfection of pTG2333, pHMG-Tat and LTR-CAT in a concentration ratio of 10:1:0.5.

The results are presented in Table 1. It can be observed that the variant TAT (Thr$^{40}$→Ala) exhibits a transdominant phenotype as defined according to the invention. it inhibits the function of the native TAT, protein by 83% and retains a small transactivating activity of 15.6%.

Example 3

Construction of the expression vector PTG2340, expression of the variant TAT (Lys$^{41}$→Glu) and characterization of the transdominant phenotype.

The vector M13TG2306 is subjected to a site-directed mutagenesis in order to replace the codon encoding the lysine (Lys) residue in position 41 of the HIV TAT protein by a codon encoding a glutamic acid (Glu) residue and to introduce silent mutations so as to create a HindIII restriction site at the level of the codon encoding residue 42 which permits a rapid identification of the mutated vectors. The oligonucleotide used is described in SEQ ID NO:5. The mutated tat gene is transferred into the vector pSG5 giving rise to pTG2340 which makes it possible to produce the variant TAT (Lys$^{41}$→Glu).

The vector pTG2340 is transiently co-transfected into HeLa cells with the vector LTR-CAT in order to determine the transactivating activity of the variant TAT (Lys$^{41}$→Glu) according to the procedure described above. At the same time, its transdominant activity is determined by co-transfection of pTG2340, pHMG-Tat and LTR-CAT in a concentration ratio of 10:1:0.5.

The results are presented in Table 1. It can be observed that the variant TAT (Lys$^{41}$→Glu) exhibits a transdominant phenotype as defined according to the invention. The transactivating activity of the variant is low (3% of the activity conferred by the native TAT protein) and it is capable of effectively inhibiting the transactivating function of the native TAT protein (97% inhibition).

It can be noted that the variant TAT (Lys$^{41}$→Glu) produced by pTG2340 and the prior art variant TAT (Lys$^{41}$→Ala) which behaves like the native TAT protein, are mutated at the same residue. According to the modification performed, the phenotype of the variant obtained can therefore be totally different. Thus, the replacement of Lys$^{41}$ by Glu, as disclosed by the Applicant, confers a transdominant phenotype on the variant generated.

Example 4

Construction of the expression vector pTG2358, expression of the variant TAT (Ile$^{45}$→Ser) and characterization of the transdominant phenotype.

The vector M13TG2306 is subjected to a site-directed mutagenesis in order to replace the codon encoding the isoleucine (Ile) residue in position 45 of the HIV TAT protein by a codon encoding a serine (Ser) residue and to create a BamHI restriction site at the level of the codon encoding residue 45 which permits a rapid identification of the mutated vectors. The oligonucleotide, used is described in SEQ ID NO:6. The mutated tat gene is transferred into the vector pSG5 giving rise to pTG2358 which makes it possible to produce the variant TAT (Ile$^{45}$→Ser).

The vector pTG2358 is transiently co-transfected into HeLa cells with the vector LTR-CAT in order to determine the transactivating activity of the variant TAT (Ile$^{44}$→Ser) according to the procedure described above. At the same time, its transdominant activity is determined by co-transfection of pTG2358, pHMG-Tat and LTR-CAT in a concentration ratio of 10:1:0.5.

The results are presented in Table 1. It can be observed that the variant TAT (Ile$^{45}$→Ser) exhibits a transdominant phenotype as defined according to the invention. It partially inhibits the function of the native TAT protein by 62.5% and retains a moderate transactivating activity of 47%.

Example 5

Construction of the expression vector pTG2348, expression of the variant TAT (Tyr→Arg) and characterization of the-transdominant phenotype.

The vector M13TG2306 in subjected to a site-directed mutagenesis in order to replace the codon encoding the tyrosine (Tyr) residue in position 47 of the HIV TAT protein by a codon encoding an arginine (Arg) residue and to create a XbaI restriction site at the level of the codon encoding residue 47 which permits a rapid identification of the mutated vectors. The oligonucleotide used is described in SEQ ID NO:7. The mutated tat gene is transferred into the vector pSG5 giving rise to pTG2348 which makes it possible to produce the variant TAT (Tyr$^{47}$→Arg).

The vector pTG2348 is transiently co-transfected into HeLa calls with the vector LTR-CAT in order to determine the transactivating activity of the variant TAT (Tyr$^{47}$→Arg) according to the procedure described above. At the same time, its transdominant activity is determined by co-transfection of, pTG2348, pHMG-Tat and LTR-CAT in a concentration ratio of 10:1:0.5.

The results are presented in Table 1. It can be observed that the variant TAT (Tyr$^{47}$→Arg) exhibits a moderate transdominant phenotype as defined according to the invention. It inhibits the function of the native TAT protein by 78% and retains a transactivating activity of 56%.

Example 6

Establishment of stable cell lines expressing a transdominant TAT variant and evaluation of their resistance to infection by the HIV virus.

Stable cell lines producing the transdominant variant TAT (Phe$^{38}$→Asp) were established in order to validate the efficacy of the variants for a possible use in vivo, for example in a gene therapy procedure. In order to evaluate the resistance of the cells to an HIV infection, it is necessary for them to be infectible by the virus, that is to say that they express the human CD$_4$ receptor at their surface.

two types of cell lines were established:

The CEM-A3 cells (ATCC CCL119) derived from human T cells, possess the CD$_4$ receptor and are therefore naturally infectible by HIV, the HeLa cells (ATCC CCL2) which are co-transfected with a ubiquitous expression vector for the human CD$_4$ receptor pTG620 in order to confer on them susceptibility to HIV infection. The vector pTG620 is derived from the introduction into the EcoRV site of the vector pHMG of an EcoRI fragment treated with the E. coli DNA polymerase klenow fragment comprising the copy DNA of the human CD$_4$ receptor (Maddon et al., Cell, 1986, 47, 333–348).

The BamHI fragment containing the gene encoding the transdominant variant TAT (Phe$^{38}$→Asp) is inserted into the BamHI site of the retroviral vector pLXSP (FIG. 5l ) generating pTC2350. The vector pLXSP is derived from pLXSN (Miller and Roseman, Biotechniques, 7, 1989, 980–988) and is obtained by the replacement of the neomycin gene by a gene conferring puromycin resistance and the 3' LTR from MSV by that from MPSV.

The plasmid DNA of pTG2350 is introduced into the CEH-A3 cells by electroporation. 20 μg of DNA purified on a cesium chloride gradient is taken up in 20 μl of PBS buffer (1 mM KH$_2$PO$_4$; 2 mM KCl 1316mM NaCl, 3 mM Na$_2$HPO$_4$). The DNA preparation is mixed with 2×10$^7$ cells resuspended in 180 μl of PBS in an electroporation tank (Biorad). The mixture is preincubated at room temperature for 19 minutes. After electroporation (Gene pulser Biorad, voltage 210 V, capacitance 960 μF), the cells are kept at room temperature for 10 minutes and they are incubated at 37° C. In 6 ml of RPMI (Gibco-BRL) in the presence of 5% CO$_2$. The puromycin-resistant CEM-A3 clones are isolated by limiting dilution (puromycin 0.5 μg/ml).

The plasmid DNA pTG2350 is co-transfected into the HeLa cells with pTG620 by the calcium phosphate transfection technique described above. The puromycin-resistant HeLa cell clones are isolated by successive subcultures (puromycin 2 μg/ml). The expression of the human CD$_4$ receptor at the surface of the cells is analyzed by fluorocytometry (FACS: Fluorescence Activated Cell Sorter, scan Becton Dickinson) by means of phycoerythrin-labeled Leu3A antibody (Becton Dickinson) directed against this receptor.

The expression of the TAT proten in the CEM-A3 cell line is detected by performing transient transfections of the vectors LTR-CAT and pHMG-Tat according to the technique described above.

Three clones, derived from the CEM-A3 cell line, resistant to puromycin and expressing the transdominant TAT variant and for which various degrees of inhibition of the native TAT protein were observed, are infected with the HIV virus. The propagation of the virus can be evaluated by measuring the reverse transcriptase activity in the culture supernatants. A 2-day shift in viral multiplication was thus detected in one of the clones of the CEK-A3 cell line expressing the transdominant variant compared with the result obtained in the CEM-A3 cells not expressing a transdominant variant. Furthermore, the reverse transcriptase activity is reduced by 90% in said clone.

What is claimed is:

1. A trans-dominant variant of the HIV-1 TAT protein which has a trans-activating activity of less than 50% compared to the native HIV-1 TAT protein and a native TAT function-inhibiting activity based on a concentration ratio of variant TAT/native TAT OF 10/1 which is greater than 50% wherein said variant is selected from the group consisting of the following variants:

(i) a variant comprising a single substitution mutation at position 38 that results in the change of the wild-type amino acid at position 38 to an amino acid having an acidic side chain which is selected from the group consisting of glutamic acid and aspartic acid;

(ii) a variant comprising a single substitution mutation at position 40 which results in the change of the wild-type amino acid at position 40 to an amino acid having a non-polar side chain which amino acid is selected from the group consisting of alanine, valine, leucine, isoleucine, proline, phenylalanine, methanine, and tryptophan;

(iii) a variant comprising a single substitution mutation at position 41 which results in the change of the wild-type amino acid at position 41 to an amino acid having an acidic side chain which amino acid is selected from the group consisting of glutamic acid and aspartic acid;

(iv) a variant comprising a single substitution mutation at position 45 which result in the change of the wild-type amino acid at Position 45 to an amino acid having an uncharged polar side chain, which amino acid is selected from the group consisting of glycine, asparagine, glutamine, cysteine, serine, threonine, and tyrosine; and (v) a variant comprising a single substitution mutation at position 47 which results in the change of the wild-type amino acid at position 47 to an arginine.

2. The TAT protein variant of claim, 1 comprising a single substitution at position 38 that results in the change of the wild-type amino acid at position 38 to an aspartic acid.

3. The TAT protein variant of claim 1, comprising a single substitution at position 40 which results in the change of the wild-type amino acid at position 40 to an alanine.

4. The TAT protein variant of claim 1, comprising a single substitution at position 41 that results in the change of the wild-type amino acid at position 41 to a glutamic acid.

5. The TAT protein variant of claim 1 comprising a single substitution at position 45 that results in the change of the wild-type amino acid at position 45 to a serine.

6. The TAT protein variant of claim 1 comprising a single substitution at position 47 that results in the change of the wild-type amino acid at position 47 to an arginine.

7. An isolated and purified cell line comprising a trans-dominant HIV-1 TAT variant according to claim 1, wherein said variant is encoded by an expression vector.

8. An isolated and purified cell line comprising a trans-dominant HIV-1 TAT variant according to claim 2, wherein said variant is encoded by an expression vector.

9. An isolated and purified cell line comprising a trans-dominant HIV-1 TAT variant according to claim 3, wherein said variant is encoded by an expression vector.

10. An isolated and purified cell line comprising a trans-dominant HIV-1 TAT variant according to claim 4, wherein said variant is encoded by an expression vector.

11. An isolated and purified cell line comprising a trans-dominant HIV-1 TAT variant according to claim 5, wherein said variant is encoded by an expression vector.

12. An isolated and purified cell line comprising a trans-dominant HIV-1 TAT variant according to claim 6, wherein said variant is encoded by an expression vector.

13. A composition of matter comprising a TAT protein variant according to claim 1 and a pharmaceutically acceptable carrier.

14. A composition of matter comprising a TAT protein variant according to claim 2 and a pharmaceutically acceptable carrier.

15. A composition of matter comprising a TAT protein variant according to claim 3 and a pharmaceutically acceptable carrier.

16. A composition of matter comprising a TAT protein variant according to claim 4 and a pharmaceutically acceptable carrier.

17. A composition of matter comprising a TAT protein variant according to claim 5 and a pharmaceutically acceptable carrier.

18. A composition of matter comprising a TAT protein variant according to claim 6 and a pharmaceutically acceptable carrier.

19. A composition of matter comprising a cell according to claim 7 and a pharmaceutically acceptable carrier.

20. A composition of matter comprising a cell according to claim 8 and a pharmaceutically acceptable carrier.

21. A composition of matter comprising a cell according to claim 9 and a pharmaceutically acceptable carrier.

22. A composition of matter comprising a cell according to claim 10 and a pharmaceutically acceptable carrier.

23. A composition of matter comprising a cell according to claim 11 and a pharmaceutically acceptable carrier.

24. A composition of matter comprising a cell according to claim 12 and a pharmaceutically acceptable carrier.

* * * * *